United States Patent [19]
Kowalski et al.

[11] Patent Number: 5,981,224
[45] Date of Patent: Nov. 9, 1999

[54] BOVINE HEAT SHOCK PROMOTER AND USES THEREOF

[75] Inventors: Jacek Kowalski; Scott Gilbert; Timothy J. Zamb, all of Saskatoon, Canada

[73] Assignee: Biostar Inc., Saskatoon, Canada

[*] Notice: This patent is subject to a terminal disclaimer.

[21] Appl. No.: 09/048,488

[22] Filed: Mar. 26, 1998

Related U.S. Application Data

[63] Continuation of application No. 08/599,825, Feb. 12, 1996, Pat. No. 5,733,745, which is a continuation of application No. 07/975,719, Nov. 10, 1992, Pat. No. 5,521,084.

[51] Int. Cl.$^6$ .............................. C12N 1/21; C12N 5/10; C12N 15/11; C12P 21/00
[52] U.S. Cl. ................ 435/69.1; 435/252.3; 435/320.1; 435/325; 435/69.3; 536/23.1; 536/24.1; 536/23.72
[58] Field of Search .................. 536/24.1, 23.1, 536/23.72; 435/320.1, 325, 252.3, 69.1, 69.3

[56] References Cited

U.S. PATENT DOCUMENTS

| | | | |
|---|---|---|---|
| 5,151,267 | 9/1992 | Babiuk et al. | 424/186.1 |
| 5,521,084 | 5/1996 | Kowalski et al. | 435/325 |
| 5,733,745 | 3/1998 | Kowalski et al. | 435/69.3 |

FOREIGN PATENT DOCUMENTS

| | | |
|---|---|---|
| 118393 | 9/1984 | European Pat. Off. . |
| 336523 | 10/1989 | European Pat. Off. . |
| WO 87/00861 | 2/1987 | WIPO . |
| WO 87/05935 | 10/1987 | WIPO . |

OTHER PUBLICATIONS

McGarry et al., Cell 42:903–911 (1985).
Collett et al., Virology 165:200–208 (1988).
Collett et al., *Virology* 165:191–199 (1988).
Craig and Gross, *Trends Bioch. Sci.* 16:135 (1991).
Cruz et al., *Biochem. Journal* 277:327–330 (1991).
Dreano et al., *Gene* 49:1–8 (1986).
George et al., "Macromolecular Sequencing and Synthesis Selected Methods and Applications," (Alan R. Liss, Inc., N.Y.) pp. 127–149 (1988).
Grosz et al., *Genomics* 14;863–868 (1992).
Hay et al., American Type Culture Collection Catalogue of Cell Lines and Hybridomas (American Type Culture Collection, Rockville, MD) p. 16 (1992).
Hightower, *Cell* 66:191–197 (1991).
Hunt and Morimoto, *Proc. Natl. Acad. Sci USA* 82:6455–6459 (1985).
Kowalski et al., *Vaccine* 11(11):1100–1107 (1993).
Li, *Int. J. Radiat. Oncol. Biol. Phys.* 11:165–177 (1985).
Fitzpatrick et al., *Virology* 173:46–57 (1985).
Moormann et al., *Virology* 177:184–198 (1990).
Schiller et al., *J. Mol. Biol.* 203:97–105 (1988).
Simcox et al., *Mol. Cell. Biol.* 5:3397–3402 (1985).
Sorger, *Cell* 65:363 (1991).
Theodorakis and Morimoto, *Mol. Cell. Biol.* 7:4357–4368 (1987).
Tikoo et al., *Journal of Virology* 64:5132–5142 (1990).
Wu et al., *Mol. Cell. Biol.* 5:330–341 (1985).
Yost et al., in *Stress Proteins in Biology and Medicine*, Morimoto et al., eds., Cold Spring Harbor Press at 379–409, (1990).

*Primary Examiner*—Johnny F. Railey, II
*Attorney, Agent, or Firm*—Robins & Associates

[57] ABSTRACT

A novel expression system using the heat-inducible bovine hsp70A promoter and associated cis-acting elements is disclosed. The system provides for the continuous production of a highly pure, authentic protein, substantially free of infectious viral and cellular protein contaminants.

39 Claims, 4 Drawing Sheets

```
      TCTTCGAGAAACTCGGGAACTTTCTGTATTTTGGCTGTCCCGGCAGTCGTGTAGC    55
        HSE
      CCTTAATTCTACTTTAAACCACCAAACTAATTTGAGCCCCGAGATCCTCTCACCG   110

CCCTACAATTAATTACAAGCCCAGGGCTGATCCTTCCAGTCGACTCGACTCCAAA   165

CTACTTGGCTGGCTGGTCGCCAGGAAACCAGAGACAGAGTGGGTGGACCTTCCCA   220
                                                      ::::
 40                                                   TTCCT-

GCCCCTCTCCCCCTCTCCTTAGGACTCCTGTTTCCTCCAGCGAATCCTAGAAGAG   275
         :::          ::    :::::  :::::::: :::::: ::::::
 45   --------------CTCA---GGGTCCCTGTCCCCTCCAGTGAATCCAGAAGAC
                                                HSE
      TCTGGAGAGTTCTGGGA--GGAGAGGCATCCAGGGCGCTGATTGGTTCCAGAAAG   328
      ::::::::::::::: :   ::  ::::  : ::  : :::::::: : :: :::
 83   TCTGGAGAGTTCTGAGCAGGGGGCGGCACTCTGGCCTCTGATTGGTCCAAGGAAG
         HSE                                 CCAAT
      CCAGGGGG-CAGGACTTGAGGCGAAACCCCTGGAATATTCCCGACCTGGCAGCCC   382
      : :::::  :::::::     :::::::::::::::::::::::::::::::::
138   GCTGGGGGGCAGGACGGGAGGCGAAACCCCTGGAATATTCCCGACCTGGCAGCCT
                                   HSE
      CACTGAGCTCGGTCATTGGCTGACGAGGGAAAAGGCGGGGCTTGATGAAGAAT    435
      :: :::::::::: ::::::::::: : ::::::::::::::: ::  :: :
193   CATCGAGCTCGGTGATTGGCTCAGAAGGGAAAAGGCGGGTCTCCGTGACGACT
              CCAAT           Pu Box       GC
      TATAAACACAGAGCCGCCTGAGGA---GA-AACAGC-AGCCTGGAGAGAGCTGATAA   487
      ::::::  : ::  ::   : ::    :: ::: ::  ::::::  :  ::::::  :
246   TATAAAAGCCCAGGGGCAAGCGGTCCGGATAACGGCTAGCCTGA-GG-AGCTGCTGC

AACTTACGGCTTAGTCCGT-GAGAGCAGCTTCCGCAGACCCGCTATCTCCAAGGA   541
       ::    : ::    :  : ::::::  ::  :::  : :::         :::  ::
301   GACAGTCCACTACCTTTTTCGAGAGTGACTCCCGTTGTCCCAAGGCTTCCCAGAG

CCGCCC---GAGG-----GGCACCAGAGCGTTCAGTTTTCGGGTTCCGAAAAGCC   588
      :   ::   ::       :::::: :  ::::  ::::: :::  :::: :: ::
356   CGAACCTGTGCGGCTGCAGGCACCGGCGCGTCGAGTTTCCGGCGTCCGGAAGGAC

CGAGCTTCTCGTCGCAGATCCTCTTCACCGATTTCAGGTTTGAAGCTTATTTCGG   643
      ::::::  :  ::::  :::::  :   :::  :: :::  :: :::: :   : :
411   CGAGCTC-TTCTCGCGGATCCAGTGTTCCGTTTCCAGCCCCCAATCTCAGAGCCG

AGCCGGAAAAG--CAGGGCACCGGCATGGCGAAAAACACAGCTATCGGCATCGAC   696
      :::::   : ::  :::::::: ::::  ::: :::  : : ::  :::::::::::
465   AGCCGACAGAGAGCAGGGAACCGC-ATGGCAAAGCCGCGGCAGTCGGCATCGAC

CTGGGCACCACCTACTCCTGCGTAGGGGTGTTCCAGCACGGCAAGGTGGAGATC    750
      ::::::::::::::::::::::::  :::::::::::  :::::::::::::::::
519   CTGGGCACCACCTACTCCTGCGTGGGGGTGTTCCAACACGGCAAGGTGGAGATC
```

BOVINE HEAT SHOCK PROMOTER AND USES THEREOF

This application is a continuation of U.S. patent application Ser. No. 08/599,825 filed on Feb. 12, 1996, U.S. Pat. No. 5,733,745, which is a continuation of application Ser. No. 07/975,719 filed on Nov. 10, 1992, now U.S. Pat. No. 5,521,084.

TECHNICAL FIELD

The present invention relates generally to recombinant gene expression systems. More particularly, the invention relates to novel methods for expressing and secreting gene products using the inducible bovine heat shock promoter. The invention is particularly useful for the production of pharmaceutically important polypeptides.

BACKGROUND OF THE INVENTION

Proteins are conveniently produced in a variety of procaryotic and eucaryotic recombinant expression systems. These systems, however, often fail to mimic natural production such that the resulting protein lacks the authentic tertiary conformation and post-translational modifications normally present. Furthermore, expression levels are frequently inadequate, particularly in virally-vectored mammalian systems. For example, in lytic systems, expression can be severely limited by lytic functions of the virus. When high expression levels are achieved, problems with cell growth and expansion can be encountered due to the cytotoxicity of the expressed proteins. Non-lytic systems often suffer from low yields, clone instability and cytotoxicity of the final product.

Inducible expression systems have been employed in an effort to overcome some of these problems. However, most of the inducible promoters currently used in such systems are either restricted to a relatively narrow range of host cells, are only partially inducible or are derived from organisms, such as tumor viruses, which are inherently dangerous. Accordingly, an inducible expression system which provides for the large scale synthesis of proteins, without the above-described concomitant problems, would be highly desirable.

One such candidate is a system using a promoter derived from a group of proteins known as the heat shock proteins (hsps). These proteins are ubiquitous, being found in all eucaryotic organisms studied to date, and are inducible by heat stress, as well as a variety of other external agents. Thus, cells respond to these inducers, such as elevated growth temperatures, by synthesizing high levels of hsps and coordinately reducing the rate of synthesis of other cellular proteins.

Hsps are divided into several groups on the basis of size of interest is the hsp70 family, so named because these proteins are approximately 70 kDa in mass. The level of synthesis of hsp70 in cells during heat shock appears to be linearly related to their thermotolerance. Li, G. C. (1985) *Int. J. Radiat. Oncol. Biol. Phys.* 11:165–177. Two human hsp70 proteins have been described—hsp70A (Wu, B., et al. (1985) *Mol. Cell. Biol.* 5:330–341; Hunt, C., and Morimoto, R. I. (1985) *Proc. Natl. Acad. Sci. USA* 82:6455–6459) and hsp70 B (Schiller, P., et al. (1988) *J. Mol. Biol.* 203:97–105). For a review of hsps, see, e.g., Morimoto et. al., eds., *Stress Proteins in Biology and Medicine* (1990) Cold Spring Harbor Press; Hightower, L. E. (1991) *Cell* 66:191–197.; Craig, E. A., and Gross, C. A. (1991) *Trends Bioch. Sci.* 16:135.

The hsp70 promoter, as well as sequences in the 5'- and 3'-untranslated regions of hsp70 gene transcripts, are responsible for regulating the level of protein and mRNA synthesis in the cell in both the induced and uninduced states (Simcox, A. A., et al. (1985) *Mol. Cell. Biol.* 5:3397–3402; Theodorakis, N. G., and Morimoto, R. I. (1987) *Mol. Cell. Biol.* 7:4357–4368; Yost, H. J., et al. (1990) in *Stress Proteins in Biology and Medicine,* Morimoto et. al., eds., *Stress Proteins in Biology and Medicine* (1990) Cold Spring Harbor Press, at 379–409). A region known as the heat shock element (HSE), is found within the first 100 bp 5' of the RNA start site of eucaryotic heat shock genes. Sorger, P. K. (1991) *Cell* 65:363. This region includes the sequence nGAAn, repeated at least two times in head-to-head or tail-to-tail orientation (nGAAnnTTCn or nTTCnnGAAn). Hsp70 genes from different species differ in the number and orientation of HSEs and in the types of other factor-binding sites found upstream. The HSE functions in stress induced promoter activation by binding a positive transactivating factor, the heat shock factor (HSF). The binding constant of this factor to the heat shock element is about a hundred fold higher than that of any other known mammalian transcription factor to its respective binding site, rendering this promoter one of the strongest.

Hsp promoters have been used to express a variety of genes. For example, Dreano, M., et al. (1986) *Gene* 49:1–8, describe the use of the human hsp70B promoter, as well as a Drosophila hsp70 promoter, to direct the heat regulated synthesis of human growth hormone, chicken lysozyme and a human influenza haemagglutinin.

EPA Publication No. 336,523 (Dreano et al., published Oct. 11, 1989) describes the in vivo expression of human growth hormone using a human hsp70 promoter.

PCT Publication No. WO 87/00861 (Bromley et al., published Feb. 12, 1987) describes the use of human and Drosophila hsp promoters having 5'-untranslated region variants.

EPA Publication No. 118,393 (Bromley et al., published Sep. 12, 1984) and PCT Publication No. WO 87/05935 (Bromley et al., published Oct. 8, 1987) describe the expression of *E. coli* β-galactosidase and human influenza haemagglutinin, using a Drosophila hsp70 promoter.

However, none of the above-described references pertains to bovine hsp promoters or to the use of these promoters to drive the expression of heterologous proteins in thermotolerant cells. Nor do any of these references describe the use of an hsp70A promoter for recombinant expression.

DISCLOSURE OF THE INVENTION

Accordingly, the present invention provides a highly efficient inducible expression system for the production of recombinant proteins. The system allows prolonged, reversible production of proteins which mimic authentic molecules, free of potentially pathogenic agents, in large, economically useful quantities.

In one embodiment, the invention is directed to an isolated bovine hsp70 promoter capable of directing the transcription of a heterologous coding sequence positioned downstream therefrom.

In another embodiment, the subject invention is directed to an isolated bovine hsp70 5'-untranslated region.

In still another embodiment, the invention is directed to a recombinant expression construct effective in directing the transcription of a selected coding sequence. The expression construct comprises:

(a) bovine hsp70 control sequences; and (b) a coding sequence operably linked to the control sequences, whereby the coding sequence can be transcribed and translated in a host cell, and at least one of the control sequences is heterologous to the coding sequence.

In particularly preferred embodiments, the bovine hsp70 control sequences in the expression construct comprise a nucleotide sequence substantially homologous and functionally equivalent to the sequence depicted at nucleotide positions 1 to 666, inclusive, of the upper strand of FIG. 2 (SEQ ID NOS:1–2).

Still further embodiments of the subject invention include host cells transformed with these constructs and methods of producing recombinant polypeptides using the host cells.

These and other embodiments of the present invention will readily occur to those of ordinary skill in the art in view of the following disclosure, or may be learned by practice of the invention.

BRIEF DESCRIPTION OF THE FIGURES

FIG. 1a shows the restriction map of the genomic insert in the λ EMBL3A clone. FIG. 1b shows the BglII-XhoI fragment subcloned in pBLUE-SCRIPT (pBS). The region indicated by the open bar is the region sequenced and shown in FIG. 2. The position of the ATG initiation codon of the hsp70 gene is indicated.

FIG. 2 (SEQ ID NOS:1–2) shows a comparison of the sequence of the 5'-upstream region and a part of the coding region of the bovine hsp70A gene (numbered on the right) with the human homolog (numbered on the left). The bovine sequence corresponds to that marked by the open bar in FIG. 1b. The human hsp70A sequence corresponds to bases 40–573 of the sequence published by Hunt, C., and Morimoto, R. I. (1985) Proc. Natl. Acad. Sci. USA 82:6455–6459. The first 40 bp of the human sequence do not significantly match any of the bovine sequence yet determined. Transcription factor binding sites, TATAA box, and translation start codon are indicated.

FIG. 3 demonstrates the heat regulated expression and secretion of bovine herpesvirus type 1 ("BHV-1") glycoproteins in transiently-transfected Madin-Darby bovine kidney ("MDBK") cells analyzed by Western blotting.

FIG. 4 shows the secretion of BHV-1 gIV by a heat inducible clone (MG4-57) of stably-transformed MDBK cells over a protracted time period.

DETAILED DESCRIPTION OF THE INVENTION

Figure 1:
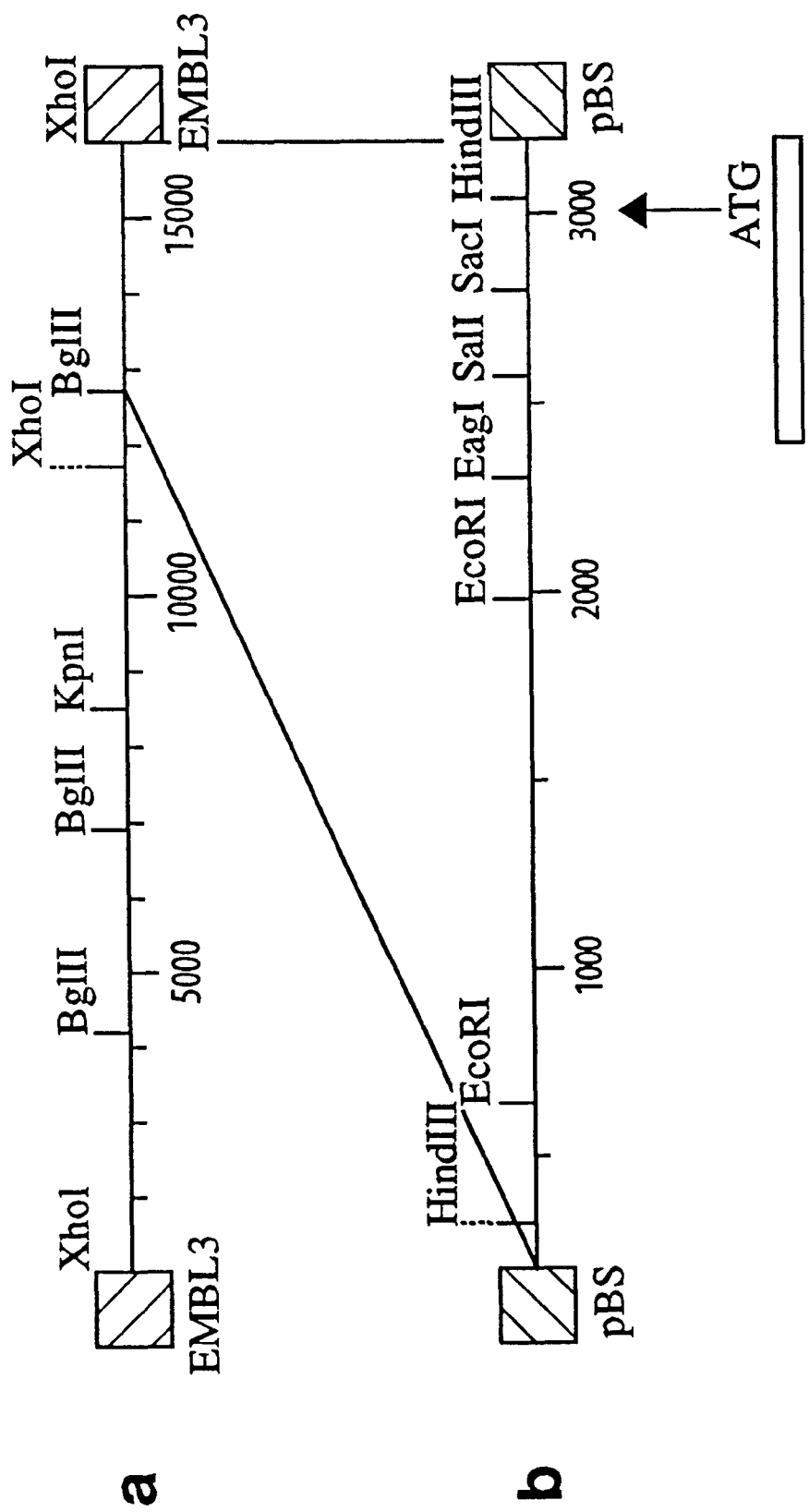
FIG. 1 shows a map of a bovine genomic hsp70 gene λ clone and derived plasmid.
Figures 3A, 3B:
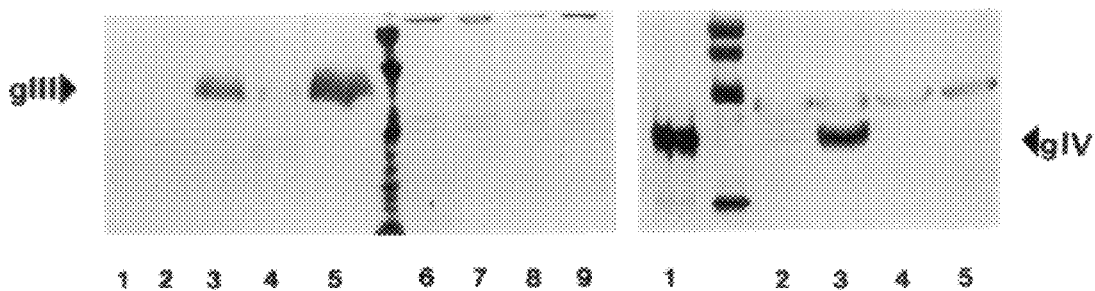
FIG. 3a shows an experiment with plasmid p3KHSPG3HU, expressing truncated BHV-1 glycoprotein III ("gIII").
FIG. 3b shows an experiment with plasmid p3KHSPG4HU, expressing truncated BHV-1 glycoprotein IV ("gIV").

The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Sambrook, Fritsch & Maniatis, *Molecular Cloning: A Laboratory Manual*, Second Edition (1989); DNA Cloning, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); Perbal, B., *A Practical Guide to Molecular Cloning* (1984); the series, *Methods In Enzymology* (S. Colowick and N. Kaplan eds., Academic Press, Inc.); and *Handbook of Experimental Immunology*, Vols. I–IV (D. M. Weir and C. C. Blackwell eds., 1986, Blackwell Scientific Publications).

All patents, patent applications and publications cited herein, whether supra or infra, are hereby incorporated by reference in their entirety.

As used in this specification and the appended claims, the singular forms "a," "tan" and "the" include plural references unless the content clearly dictates otherwise.

A. Definitions

In describing the present invention, the following terms will be employed, and are intended to be defined as indicated below.

A "thermotolerant cell or cell line" is a cell or cell line obtained from an organism with a normal body temperature above 37° C. It has been shown that thermotolerance of cultured cells is related to the normal body temperature of the species from which they are derived. Raaphorst, G. P., et al. (1979) *Cancer Res.* 39:396. Generally such cells can survive and divide at temperatures above 37° C., for a number of hours and still maintain growth rates substantially the same as rates seen when the same cell is grown at 37° C.

By "bovine hsp70 promoter" is meant a DNA regulatory region derived from a bovine hsp70 gene which is capable of binding RNA polymerase and initiating transcription of a downstream (3'-direction) coding sequence. A "bovine hsp70 promoter" encompasses both promoters with identity to an hsp70 promoter isolated from a bovine species, as well as one which is substantially homologous and functionally equivalent thereto (as defined below). The human and Drosophila hsp70 promoters are specifically excluded from this definition. For purposes of defining the present invention, the promoter sequence is bound at the 3'-terminus by the transcriptional start site (but does not necessarily include the site which can be provided by the 5'-UTR, described further below). The transcriptional start site is approximately 30 bps downstream (3'-direction) from the TATA box. The promoter extends upstream (5'-direction) to include the minimum number of bases or elements necessary to initiate transcription at levels detectable above background. Within the promoter sequence will be found protein binding domains (consensus sequences), responsible for binding various transcription factors and the TATA box for binding RNA polymerase. The bovine hsp70 promoter will also include one or more heat shock elements for binding heat shock factor during heat stress. A bovine hsp70A promoter sequence, isolated and cloned as described in the examples, is shown in FIG. 2 (SEQ ID NOS:1–2) and appears to include at least nucleotides 1 to 441 of the figure.

A "bovine hsp70 5'-UTR" refers to an untranslated region of nucleotides from the bovine hsp70 gene, bound at its 3'-end by the ATG codon and extending upstream (in the 5' direction) to the hsp70 transcription start site. As explained above, this site is located approximately 30 nucleotides downstream from the TATA box.

Two DNA or polypeptide sequences are "substantially homologous" when at least about 80% (preferably at least about 90%, and most preferably at least about 95%) of the nucleotides or amino acids match over a defined length of the molecule. As used herein, substantially homologous also refers to sequences showing identity to the specified DNA or polypeptide sequence. It is to be understood that a sequence of nucleotides or amino acids "substantially homologous" to a sequence of nucleotides or amino acids of bovine hsp70

DNA does not encompass the corresponding human or Drosophila hsp70 nucleotide or amino acid sequences. DNA sequences that are substantially homologous can be identified in a Southern hybridization, experiment under, for example, stringent conditions, as defined for that particular system. Defining appropriate hybridization conditions is within the skill of the art. See, e.g., Sambrook et al., supra; *DNA Cloning*, vols I & II, supra; *Nucleic Acid Hybridization*, supra.

A sequence "functionally equivalent" to a bovine hsp70 sequence is one which functions in the same manner as the corresponding hsp70 sequence. Thus, a promoter sequence "functionally equivalent" to the bovine hsp70 promoter described herein is one which is capable of directing transcription of a downstream coding sequence above background levels.

A DNA "coding sequence" or a "nucleotide sequence encoding" a particular protein, is a DNA sequence which is transcribed and translated into a polypeptide in vivo or in vitro when placed under the control of appropriate regulatory sequences. The boundaries of the coding sequence are determined by a start codon at the 5'-(amino) terminus and a translation stop codon at the 3'-(carboxy) terminus. A coding sequence can include, but is not limited to, procaryotic sequences, cDNA from eucaryotic mRNA, genomic DNA sequences from eucaryotic (e.g., mammalian) sources, viral RNA or DNA, and even synthetic nucleotide sequences. A transcription termination sequence will usually be located 3' to the coding sequence.

DNA "control sequences" refers collectively to promoter sequences, polyadenylation signals, transcription termination sequences, upstream regulatory domains, enhancers, and the like, untranslated regions, including 5'-UTRs and 3'-UTRs, which collectively provide for the transcription and translation of a coding sequence in a host cell.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A control sequence "directs the transcription" of a coding sequence in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. In eucaryotic cells, a stably transformed cell is generally one in which the exogenous DNA has become integrated into the chromosome so that it is inherited by daughter cells through chromosome replication, or one which includes stably maintained extrachromosomal plasmids. This stability is demonstrated by the ability of the eucaryotic cell to establish cell lines or clones comprised of a population of daughter cells containing the exogenous DNA.

A "heterologous" region of a DNA construct is an identifiable segment of DNA within or attached to another DNA molecule that is not found in association with the other molecule in nature. For example, a sequence encoding a bovine protein other than an hsp is considered a heterologous sequence when linked to an hsp bovine promoter. Similarly, a sequence encoding an hsp will be considered heterologous when linked to an hsp promoter with which it is not normally associated. Another example of a heterologous coding sequence is a construct where the coding sequence itself is not found in nature (e.g., synthetic sequences having codons different from the native gene). Likewise, a chimeric sequence, comprising a heterologous structural gene and a gene encoding an hsp or a portion of an hsp, linked to an hsp promoter, whether derived from the same or a different hsp gene, will be considered heterologous since such chimeric constructs are not normally found in nature. Allelic variation or naturally occurring mutational events do not give rise to a heterologous region of DNA, as used herein.

The term "immunogenic polypeptide" refers to a polypeptide which elicits antibodies that neutralize viral or bacterial infectivity (depending on the antigen in question), and/or mediate antibody-complement or antibody dependent cell cytotoxicity to provide protection of an immunized host. An "immunogenic polypeptide" as used herein, includes the full length (or near full length) sequence of the antigen in question, or an immunogenic fragment thereof. By "immunogenic fragment" is meant a fragment which includes one or more epitopes and thus elicits antibodies that neutralize viral or bacterial infectivity, and/or mediate antibody-complement or antibody dependent cell cytotoxicity to provide protection of an immunized host. Such fragments will usually be at least about 5 amino acids in length, and preferably at least about 10 to 15 amino acids in length. There is no critical upper limit to the length of the fragment, which could comprise nearly the full length of the protein sequence, or even a fusion protein comprising fragments of two or more epitopes. For example, the BHV-1 gIII and gIV immunogenic polypeptides exemplified herein are fragments lacking the transmembrane binding domains of the proteins, thereby facilitating secretion of the expressed product.

B. General Methods

The present invention is based on the isolation and characterization of a bovine hsp70 promoter and the use of this promoter in an expression system for the production of heterologous proteins. The promoter is inducible. Thus, large quantities of desired proteins can be recombinantly produced by subjecting transformed cells to elevated temperatures, as well as to other known inducers of the promoter. The promoter can be used to direct the transcription of a desired protein in a wide variety of cell types. If desired, a thermotolerant cell line can be used, thereby increasing production efficiency, as well as the longevity of the host cell during recombinant production. Cis-acting control elements can be conveniently associated with the bovine hsp70 promoter in order to optimize expression of the structural gene associated therewith. These regulatory elements direct the efficient expression of the structural gene during heat shock. If proteins produced in the system are either naturally secreted or engineered to be, the transformed cells can survive and produce the protein product for protracted time periods, further increasing yields. The system allows for the production of a desired protein in an authentic configuration, with authentic post-translation modifications, in a relatively pure form and in economically useful amounts.

The hsp70 promoter of the present invention can be isolated from a bovine genomic library using an appropriate probe and cloned for future use. Similarly, the sequence can be produced synthetically, based on the sequence depicted in FIG. 2 (SEQ ID NOS:1–2), using known methods of polynucleotide synthesis. See, e.g. Edge, M.D., *Nature* (1981) 292:756; Nambair, et al. *Science* (1984) 223:1299; Jay, Ernest, *J. Biol. Chem.* (1984) 259:6311.

For purposes of the present invention, the bovine hsp70A promoter was isolated by screening a bovine genomic library with a human hsp70A probe, as described further below. The promoter appears to include at least the nucleotides depicted at positions 1 to 441 of FIG. 2 (SEQ ID NOS:1–2). A TATAAA box (presumed to bind transcription factor IID) is located at positions 436–441 of FIG. 2 (SEQ ID NOS:1–2). Two CCPAT boxes (the binding sites for the CCAAT box-binding transcription factor, CTF) are located at positions 314 and 397, respectively, of the figure. A purine rich element and GC element (for binding Sp1 factor) is found at position 408. Three regions including heat shock elements appear to be present at positions 3–24, 265–287 and 350–372.

The bovine hsp70 promoter, or a functional portion thereof, can be used to direct the transcription of a heterologous coding sequence when operably linked thereto. The entire promoter sequence need not be present so long as at least one heat shock element, as well as the transcription initiation site and the RNA polymerase binding site, are present. Accordingly, a promoter can be engineered to include only these necessary sequences. Generally, for use in the present expression system, a sequence of nucleotides substantially homologous and functionally equivalent to nucleotides found at about positions 350 to 441, encompassing one heat shock element, more preferably about 265 to 441, encompassing two heat shock elements, and even nucleotides 1 to 441 and regions extending upstream from position 1 and downstream from position 441, will be used to direct the transcription of the desired heterologous coding sequence.

In order to achieve efficient expression using the bovine hsp70 promoter, it is desirable to include an hsp70 5'-UTR region in the present system. This region is bound at its 3'-end by the ATG codon and extends upstream (in the 5' direction) to the hsp70 transcription start site. As explained above, the transcription start site is located approximately 30 nucleotides downstream from the TATA box. Thus, the bovine hsp70A 5'-UTR appears to encompass approximately 190 to 200 nucleotides upstream of the ATG codon depicted in FIG. 2 (SEQ ID NOS:1–2). This region shows approximately 65% sequence homology to the corresponding human hsp70A 5'-UTR.

The hsp70 5'-UTR region used need not be derived from a bovine host, but can be derived from another corresponding eucaryotic gene, such as from a human hsp70 gene, an insect hsp70 gene, such as from Drosophila, or any other eucaryotic hsp70 gene. If the bovine hsp70A promoter is used, it is preferable to use a corresponding hsp70A 5'-UTR (again, not necessarily from a bovine source). However, 5'-UTRs derived from hsp70 B genes will also find use in systems utilizing the hsp70A promoter.

If an homologous 5'-UTR is utilized, it is generally provided as part of the isolated bovine hsp70 promoter and associated sequences and no further manipulation is necessary. The 5'-UTR can also be synthetically produced, based on known 5'-UTR sequences, and ligated to the hsp70 promoter sequence. Similarly, the 5'-UTR can be isolated from, or the promoter construct added to, a plasmid bearing the 5'-UTR sequence, using restriction enzymes and procedures. Site specific DNA cleavage is performed by treatment with a suitable restriction enzyme (or enzymes), under conditions which are generally understood in the art, and the particulars of which are specified by the manufacturer of these commercially available enzymes. See, e.g., New England Biolabs, Product Catalog. If desired, size separation of the cleaved fragments may be performed by polyacrylamide gel or agarose gel electrophoresis, using standard techniques. A general description of size separations is found in *Methods in Enzymology* (1950) 65:499–560. The 5'-UTR and promoter sequence can then be ligated to each other using known techniques.

Sequences derived from the 3'-UTR, an untranslated region flanking the 3'-end of the hsp70 structural gene, can also be used in conjunction with the present system and can be placed downstream from the coding region to increase expression efficiency thereof. The 3'-UTR appears to stabilize mRNA. As with the 5'-UTR, the 3'-UTR need not necessarily be derived from a bovine hsp gene. Rather, the 3'-UTR can come from any corresponding hsp70 gene or even the gene to be expressed, provided that the gene includes a 3'-UTR. The examples herein describe the use of a human hsp70A 3'-UTR and a Drosophila 3'-UTR, respectively, in combination with a bovine hsp70A promoter and 5'-UTR, to direct the expression of a heterologous coding sequence. The 3'-UTR is ligated 3' to the desired structural gene using techniques known in the art.

Markers and amplifiers can also be employed in the subject expression systems. A variety of markers are known which are useful in selecting for transformed cell lines and generally comprise a gene whose expression confers a selectable phenotype on transformed cells when the cells are grown in an appropriate selective medium. Such markers for mammalian cell lines include, for example, the bacterial xanthine-guanine phosporibosyl transferase gene, which can be selected for in medium containing mycophenolic acid and xanthine (Mulligan et al. (1981) *Proc. Natl. Acad. Sci. USA* 78:2072–2076), and the aminoglycoside phosphotransferase gene (specifying a protein that inactivates the antibacterial action of neomycin/kanamycin derivatives), which can be selected for using medium containing neomycin derivatives such as G418 which are normally toxic to mammalian cells (Colbere-Garapin et al. (1981) *J. Mol. Biol.* 150:1–14). Useful markers for other eucaryotic expression systems, are well known to those of skill in the art.

Expression can also be amplified by placing an amplifiable gene, such as the mouse dihydrofolate reductase (dhfr) gene adjacent to the coding sequence. Cells can then be selected for methotrexate resistance in dhfr-deficient cells. See, e.g. Urlaub et al. (1980) *Proc. Natl. Acad. Sci. USA* 77:4216–4220; Rungold et al. (1981) *J. Mol. and Appl. Genet.* 1:165–175.

The above-described system can be used to direct the expression of a wide variety of procaryotic, eucaryotic and viral proteins, including, for example, viral glycoproteins suitable for use as vaccine antigens, immunomodulators for regulation of the immune response, hormones, cytokines and growth factors, as well as proteins useful in the production of other biopharmaceuticals.

The present system is particularly useful for the production of bovine viral antigens, such as, but not limited to, antigens derived from bovine herpesvirus (BHV-1), bovine viral diarrhea virus (BVDV), bovine respiratory syncytial virus, bovine rotavirus, bovine coronavirus and bovine parainfluenza virus. A number of protective antigens from these viruses are known. For example, in the case of BHV-1, the viral envelope glycoproteins gI, gIII and gIV have been isolated as well as recombinantly produced and have been shown to be effective protective antigens. (See, e.g. Babiuk, L. A., et al. (1987) Virology 159:57–66 and U.S. Pat. No. 5,151,267, for a description of the isolation and cloning of these antigens, respectively, hereby incorporated by reference in their entirety). Similarly, monoclonal antibody analysis of gp53 from BVDV indicates that antibodies thereto possess virus neutralizing activity. Deregt, D., et al. (1990) *Can. J. Vet. Res.* 54:343–348 and the nucleotide sequence for gp53 is known (Collett, M. et al. (1988) *Virology* 165:191–199). Accordingly, the present invention provides a method for efficiently producing these important antigens.

The gene sequences encoding the desired protein can be isolated or obtained recombinantly, using known techniques. Alternatively, DNA sequences encoding the proteins of interest can be prepared synthetically rather than cloned. The DNA sequence can be designed with the appropriate codons for the particular amino acid sequence. In general, one will select preferred codons for efficient expression in the intended host. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

It may also be desirable to produce mutants or analogs of the proteins of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning,* Vols. I and II, supra; *Nucleic Acid Hybridization,* supra.

For purposes of the present invention, it is particularly desirable to further engineer the coding sequence to effect secretion of the polypeptide from the host organism. This enhances clone stability and prevents the toxic build up of proteins in the host cell so that expression can proceed more efficiently. Homologous signal sequences can be used for this purpose with proteins normally found in association with a signal sequence. Additionally, heterologous leader sequences which provide for secretion of the protein can be added to the constructs. Preferably, processing sites will be included such that the leader fragment can be cleaved from the protein expressed therewith. (See, e.g., U.S. Pat. No. 4,336,246 for a discussion of how such cleavage sites can be introduced). The leader sequence fragment typically encodes a signal peptide comprised of hydrophobic amino acids.

The choice of an appropriate leader will depend on the cell type used to express the protein. For example, sequences from genes encoding human a-interferon (Maeda et al. *Nature* (1985) 315:592), human gastrin-releasing peptide (Lebacq-Verheyden et al. (1988) *Molec. Cell. Biol.* 8:3129), human IL-2 (Smith et al. (1985) *Proc. Natl. Acad. Sci. USA* 82:8404), mouse IL-3 (Miyajima et al. (1987) *Gene* 58:273), and human glucocerebrosidase (Martin et al. (1988) *DNA* 7:99), will provide for secretion of a heterologous protein in mammalian cells. These sequences can also be used to provide for secretion in insect host cells, as can DNA encoding genes for secreted insect or baculovirus proteins, such as the baculovirus gp67 gene. For expression in bacteria, DNA encoding suitable signal sequences can be derived from genes for secreted bacterial proteins, such as the *E. coli* outer membrane protein gene (ompA) (Ghrayeb et al. (1984) *EMBO J.* 3:2437) and the *E. coli* alkaline phosphatase signal sequence (phoA) (Oka et al. (1985) *Proc. Natl. Acad. Sci. USA* 82:7212). (See, also, U.S. Pat. No. 4,336,336). The signal sequence of the alpha-amylase gene from various Bacillus strains can be used to secrete heterologous proteins from *B. subtilis* (Palva et al. (1982) *Proc. Natl. Acad. Sci. USA* 79:5582; EPO Publication No. 244, 042). Finally, secretion in yeast can be directed by, i.e., the yeast invertase gene (EPO Publication No. 012,873; and the α-factor gene (U.S. Pat. Nos. 4,546,083, 4,588,684 and 4,870,008).

For some proteins, particularly viral glycoproteins, secretion can be effected by deleting all or portions of the transmembrane binding domains that might be present, thereby eliminating or substantially decreasing transmembrane binding and enhancing secretion. Such an approach is described in, e.g., Motz, M., et al. (1987) *Gene* 58:149–154); and Spaete et al. (1990) *J. Virol.* 64:2922–2931.

Alternatively, molecules known to aid in the egress of the expression product from the cell can be coexpressed with the desired protein. See, e.g., Hutchinson et al. (1992) *J. Virol.* 66:2240–2250.

Once the coding sequences for the desired proteins have been prepared or isolated, an expression vector is constructed so that the particular coding sequence is located in the vector downstream from the bovine hsp70 promoter and the 5'-UTR, if present. Accordingly, the preferred constructs of the present invention will generally include, in order, a bovine hsp70 promoter sequence including a transcription start site, an hsp70 5'-UTR, a consensus sequence coding for translation initiation, a gene sequence coding for a desired protein engineered so that the protein will be secreted, and a 3'-UTR. Additional intervening nucleotide sequences can also be present so long as transcription and translation of the desired coding sequence is not disrupted.

The positioning and orientation of the coding sequence with respect to the control sequences is such that the coding sequence is transcribed under the direction of the control sequences (i.e., RNA polymerase which binds to the DNA molecule at the control sequences transcribes the coding sequence). Modification of the sequences encoding the particular protein of interest may be desirable to achieve this end. For example, in some cases it may be necessary to modify the sequence so that it can be attached to the control sequences with the appropriate orientation; i.e., to maintain the proper reading frame. The control sequences and other regulatory sequences may be ligated to the coding sequence prior to insertion into a vector. Alternatively, the coding sequence can be cloned directly into an expression vector which already contains the control sequences and an appropriate restriction site.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, as well as others. Similarly, bacterial hosts such as *E. coli, Bacillus subtilis,* and *Streptococcus spp.,* will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica.* Insect cells for use with baculovirus expression vectors include, inter alia, *Aedes aegypti, Autographa californica, Bombyx mori, Drosophila melanogaster, Spodoptera frugiperda,* and *Trichoplusia ni.*

It may be desirable to use a cell line homologous to the species in which the protein is to be used, thereby assuring structural authenticity and guaranteeing a product free of heterologous interfering contaminants. Furthermore, it is particularly preferable to use a thermotolerant cell line to produce the desired protein when heat is used as the inducing agent. Such a cell can withstand prolonged elevated temperatures, allowing induction of the heat shock promoter and the concomitant production of the desired protein for an extended period of time without cell death. A number of thermotolerant cell lines are known in the art and will generally be derived from organisms that have normal body temperatures above 37° C. Thus, cells derived from bovine species (having a normal body temperature of 39° C.), such as MDBK cells, will find use in the subject invention, as will cell lines derived from porcine (having a normal body temperature of 39° C.), muntjac (having a body temperature of 38.5° C.), and other species.

The transformation procedure used depends upon the host to be transformed. Mammalian cells can conveniently be transformed using, for example, DEAE-dextran based procedures, calcium phosphate precipitation (Graham, F. L. and Van der Eb, A. J. (1973) *Virology* 52:456–467), protoplast fusion, liposome-mediated transfer, polybrene-mediated transfection and direct microinjection of the DNA into nuclei. Bacterial cells will generally be transformed using calcium chloride, either alone or in combination with other divalent cations and DMSO (Sambrook, Fritsch & Maniatis, *Molecular Cloning: A Laboratory Manual, Second Edition* (1989)). DNA can also be introduced into bacterial cells by electroporation. Methods of introducing exogenous DNA into yeast hosts typically include either the transformation of spheroplasts or transformation of intact yeast cells treated with alkali cations.

Proteins are then produced by growing the transformed host cells in suitable media and under conditions that will provide for expression of the same. Such conditions are known or will readily be apparent to those of skill in the art. It has been found that growth in serum-free medium, with changes every 24 hours, provides dramatically increased yields of proteins. Production of the desired protein is induced by subjecting the transformed cells to an agent known to induce the hsp promoter. Such agents include, for example, heat, metal ions, such as Cd, Zn and Cu, azetidine, forskolin, prostaglandin PGA2, adenovirus ElA protein, amino acid analogs, certain ionophores, ethanol, hydrogen peroxide and inhibitors of mitochondrial function.

A particularly preferred method of induction is the use of heat. Thus, the hsp promoter is induced by increasing the ambient temperature of the cells during growth, generally in the late stationary phase, to a temperature above 37° C. Generally, cells will be maintained at a temperature of 38 to 45° C., more preferably 39 to 44° C. and most preferably 40 to 43° C., for a period of 1 to 12 hours, more preferably 4 to 6 hours, and most preferably 6 hours. Additionally, temperatures can be elevated periodically, i.e. for 1 to 10 hours a day, more preferably 3 to 6 hours a day, for a period of 1 to 21 days or more. Other suitable temperatures and time periods can be readily determined by one of skill in the art to assure the efficiency of the hsp70 promoter, thereby maximizing production levels of the desired product.

The protein is then isolated from the host cells and purified. If the expression system secretes the protein into growth media, the protein can be used directly or purified from the media. If the protein is not secreted, it is isolated from cell lysates. The selection of an appropriate recovery method is within the skill of the art.

The constructs can also be used in gene therapy or nucleic acid immunization, to direct the production of the desired gene product in vivo, by administering the expression constructs directly to a subject for the in vivo translation thereof. See, e.g. EPA Publication No. 336,523 (Dreano et al., published Oct. 11, 1989). Alternatively, gene transfer can be accomplished by transfecting the subject's cells or tissues with the expression constructs ex vivo and reintroducing the transformed material into the host. The constructs can be directly introduced into the host organism, i.e., by injection (see International Publication No. WO/90/11092; and Wolff et al., (1990) *Science* 247:1465–1468). Liposome-mediated gene transfer can also be accomplished using known methods. See, e.g., Hazinski et al., (1991) *Am. J. Respir. Cell Mol. Biol.* 4:206–209; Brigham et al. (1989) *Am. J. Med. Sci.* 298:278–281; Canonico et al. (1991) *Clin. Res.* 39:219A; and Nabel et al. (1990) *Science* 249:1285–1288. Targeting agents, such as antibodies directed against surface antigens expressed on specific cell types, can be covalently conjugated to the liposomal surface so that the nucleic acid can be delivered to specific tissues and cells for local administration. Following introduction of the expression constructs into the host organism, the animals can be heat treated to stimulate production of the desired protein using, i.e., a ventilated incubator, as described in EPA Publication No. 336,523 (Dreano et al., published Oct. 11, 1989). Alternatively, animals can be exposed to fever inducing agents or other stressors, in order to induce the hsp promoter.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

Enzymes were purchased from commercial sources, and used according to the manufacturers' directions. Radionucleotides and nitrocellulose filters were also purchased from commercial sources.

In the cloning of DNA fragments, except where noted, all DNA manipulations were done according to standard procedures. See Sambrook et al., supra. Restriction enzymes, $T_4$ DNA ligase, *E. coli* DNA polymerase I, Klenow fragment, and other biological reagents were purchased from commercial suppliers and used according to the manufacturers' directions. Double stranded DNA fragments were separated on agarose gels.

Cells and DNA Transfections

Madin-Darby bovine kidney (MDBK) cells (ATCC Accession No. CCL22) were propagated in minimal essential medium (MEM) supplemented with 10% fetal bovine serum. Transient DEAE-dextran-mediated DNA transfections were performed as described by Kriegler (Kriegler, M., (1990) *Gene Transfer and Expression* (Stockton Press)). Stable transfections were performed using 5 µg of DNA and 40 µg of Lipofectin (Felgner, P. L., et al. (1987) *Proc. Natl. Acad. Sci. USA* 84:7413–7417) per $4 \times 10^6$ cells. Neomycin-resistant clones (about 20/µg DNA) were selected by growth in the presence of 666 μg/ml G418 (Fehler, F., et al. (1992) *J. Virol.* 66:831–839, and maintained in 400 μg/ml.

Monoclonal Antibody Analysis of Secreted gIV

Indirect ELISA's were used to determine the yields of gIV as previously described (van Drunen-Littel-van den Hurk, S., et al., supra). The antigenic properties of truncated gIV secreted by MDBK cells were assessed in an indirect ELISA assay using media containing equivalent amounts of gIV from transfected MDBK cells and recombinant vaccinia virus infected BSC-1 cells, serially diluted and adsorbed to plates. The reactivity of vaccinia-produced and BHV-1-produced full-length gIV has been previously compared and found to be identical (van Drunen-Littel-van den Hurk, et al. Vaccine (In Press)). Individual or mixed gIV-specific monoclonal antibodies, followed by horseradish peroxidase-conjugated goat anti-mouse IgG were used for detection as previously described (van Drunen-Littel-van den Hurk, S., et al. (1984), supra; Hughes, G., et al., supra).

EXAMPLE 1

Cloning and Identification of the Bovine hsp70 Promoter

A total of $3 \times 10^6$ plaques of a bovine genomic library in λ EMBL3A (Frischauf, A. M. et al. (1983) *J. Mol. Biol.* 170:827) were screened at high stringency with a probe produced from a human hsp70 cDNA clone, pH2.3 (Wu, B., et al. (1985) *Mol. Cell. Biol.* 5:330–341). Five positive clones were selected and amplified. Three of these clones were unstable, since the λ phage was lost upon passage. The two remaining clones were identical and therefore likely to be clonally related. One of these was selected for further analysis. The restriction map of the genomic insert in this clone is shown in FIG. 1a. Southern blot analysis using a fragment of the human hsp70 cDNA clone was used to identify a fragment of the bovine genome clone with homology to the 5' end of the human hsp70 mRNA. This BglII-XhoI fragment was subcloned into pBS KSII+ (Stratagene; Alting-Mees, M. A., and Short, J. M. (1989) *Nucleic Acids Res.* 17:9494) for more detailed restriction enzyme analysis and sequencing.

DNA inserts in pBS KSII+ were sequenced as denatured double-stranded templates using a T7 sequencing kit (Pharmacia) and $^{35}$S-dATP (Amersham). Reaction products were analyzed by standard procedures. Data were analyzed and compared to GenBank files with sequence analysis software (IBI, Intelligenetics Inc.). All DNA sequences were determined by reading the template at least once in each direction.

The entire 1315 bp EcoRI-XhoI fragment shown between positions 2000 and 3300 in FIG. 1b was sequenced using this procedure. The sequence of the last 750 bp is shown in FIG. 2 (SEQ ID NOS:1–2) where it is compared to the corresponding region of the human hsp70A gene. The sequence from positions 667–750 constitutes a partial open reading frame. Translation of the sequence revealed that 25 of the 28 encoded amino acids are identical to the first 28 amino acids of human hsp70A protein (Hunt, C., and Morimoto, R. I. (1985) *Proc. Natl. Acad. Sci. USA* 82:6455–6459). The TATAAA box (presumed transcription factor IID binding site) is located at position 436. The human and bovine promoter appear to share approximately 70% homology over the −79 and +20 positions. The 5'-UTR of the bovine mRNA is approximately 200 nucleotides long versus 215 for the human hsp70 mRNA and shares 60% homology with the human RNA of this region. The general organization of the promoter is similar to the human hsp70A promoter (Williams, G. T. and Morimoto, R. I. (1990) *Mol. Cell. Biol.* 10:3125; Abravaya, et al. (1991) *Mol. Cell Biol.* 11:586–592). The relative placement of the heat shock elements (heat shock factor binding sites, HSE) CCAAT box [CCAAT-box binding transcription factor (CTF) binding site], purine-rich element, and GC element (Sp1 factor binding site) between positions 315 and the TATAAA element is the same as the placement of these regions in the human promoter, with 86% sequence identity over this region.

The consensus heat shock element is currently defined as three or more perfect and imperfect repeats of the sequence NGAAN in a head-to-head or head-to-tail orientation (Lis, J. T., et al., (1990) in *Stress Proteins in Biology and Medicine,* Morimoto, R. I., et al., eds. (Cold Spring Harbor Press)). The bovine hsp70 upstream region has three sites that meet these criteria. Two occur at position 265–287 and at position 350–372 where the bovine and human sequences are almost identical. The NGAAN repeats in the latter of these two have been shown to be protected in in vivo footprinting experiments (Abravaya, K., et al., supra). A second cluster of NGAAN elements is found in the bovine sequence at position 3–24 in the region for which there is no corresponding human sequence available. Three of the 5 NGAAN-type repeats in this region have the correct spacing with respect to each other for a consensus heat shock element (position 12–24).

These results show that the promoter region of the bovine homolog of the human hsp70A gene has been a isolated and sequenced. This gene is similar to the human hsp70A gene. The first 28 amino acids of the bovine hsp protein show 90% identity with that of the human hsp70 protein. The promoter region shows conservation of recognizable transcription factor binding sites and their spacing relative to one another (FIG. 2 (SEQ ID NOS:1–2)).

EXAMPLE 2

Expression Plasmid Construction For BHV-1 gIII and gIV

The ability of the bovine hsp70A heat shock promoter to direct the expression of a heterologous protein in a construct containing the bovine hsp70A 5'-UTR and a human hsp70A 3'-UTR, was tested using sequences encoding secreted forms of two BHV-1 glycoproteins as follows. After locating the translation initiation codon of the hsp70 open reading frame by sequencing, primers were synthesized for a polymerase chain reaction (PCR). The PCR produced a 530 bp promoter fragment starting with the SalI site shown in FIG. 1b and terminating with an NcoI site that incorporates the ATG initiation codon of the hsp70A gene. Plasmids with longer upstream regions were made by rejoining this fragment to upstream hsp70 fragments via the SalI site.

The BHV-1 gIII gene coding for a secreted form of the protein was obtained from a plasmid where a linker with stop codons in all three reading frames and an SpeI site had been inserted into the SplI site immediately upstream of the transmembrane anchor, terminating the protein at amino acid 465 (Fitzpatrick, D., et al. (1989) *Virology* 173:46–57). A human hsp70A 3'-UTR fragment with SpeI and ClaI termini was obtained from plasmid pH2.3 (Wu, B., et al. (1985) *Mol. Cell. Biol.* 5:330–341) by PCR. This was placed behind the truncated gIII coding sequence creating plasmid p3KHSPG3HU. This plasmid contained 3 kb of bovine hsp70 upstream sequence, including a bovine hsp70 5'-UTR, with the BHV-1 protein start codons in precisely the same location as that of the bovine hsp70 protein.

Figure 4A:
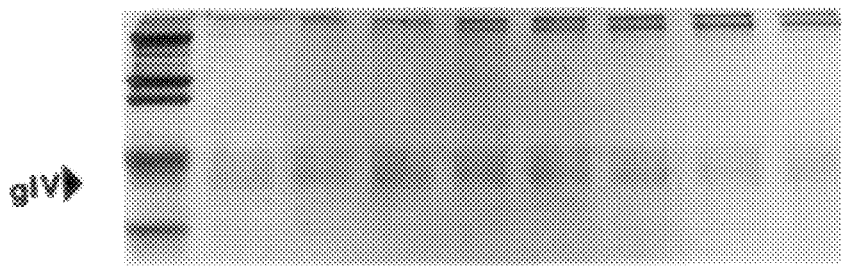
FIG. 4a is a depiction of a Coomassie blue-stained gel of culture medium.
Figure 4B:
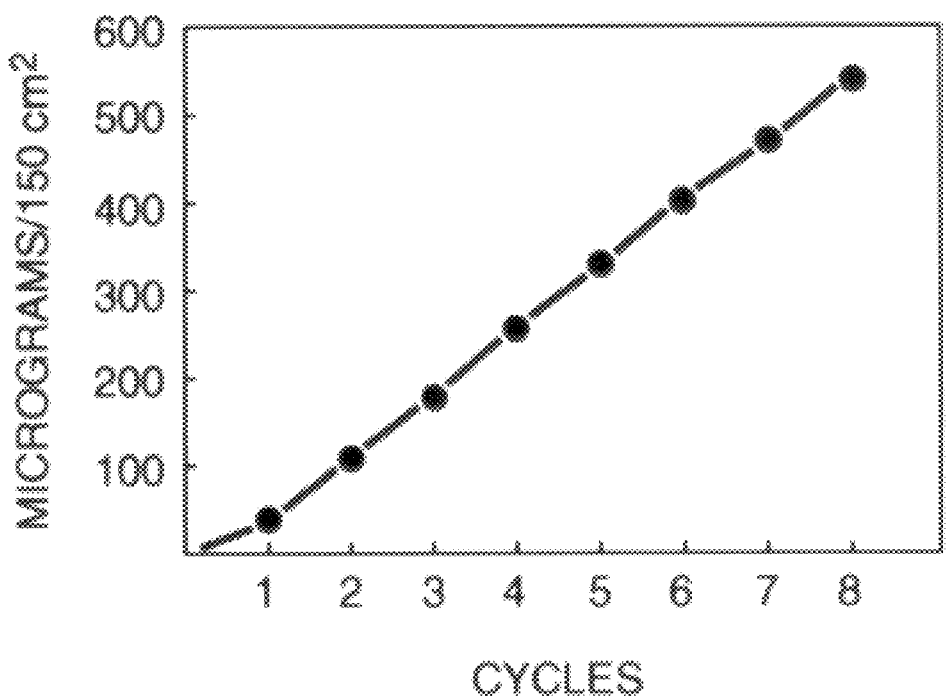
FIG. 4b shows a quantitative ELISA determination of gIV protein in media from successive daily collections plotted cumulatively.

The DNA fragment coding for a secreted form of BHV-1 gIV was obtained by modifying the 5'-end to an NcoI site at the start codon and by inserting a 3-frame stop codon linker at the SacII site immediately upstream of the transmembrane anchor terminating the protein at amino acid 320 (Tikoo, T. K., et al. (1990) *J. Virol.* 64:5132–5142). This fragment was used to replace the gIII sequences in p3KHSPG3HU, creating p3KHSPG4HU.

Plasmids for the generation of stably-transfected cell lines were constructed by inserting the cassette for the expression of aminoglycoside phosphotransferase gene from pSV2NEO (Southern, P. J., and Berg, P., (1982) *Molecular and Applied Genetics* 1:327–341) into the constructs described above, immediately behind the human hsp70 3'-UTR, yielding plasmids pG3HUNEO and pG4HUNEO (ATCC Accession Nos. 69075 and 69076, respectively), including the coding sequences for truncated gIII and gIV, respectively.

The DNA backbone for all these constructs was provided by the plasmid pPOL26 (George, H. J., et al. (1987) Biotechnology 5:600–603).

EXAMPLE 3

Expression of BHV-1 gIII and gIV using Plasmids p3KHSPG3HU and p3KHSPG4HU

Transient assays for expression and secretion of the BHV-1 glycoproteins from plasmids p3KHSPG3HU and p3KHSPG4HU, harboring the gIII and gIV genes, respectively, driven by the bovine hsp70A promoter and 5'-UTR, and a human hsp70A 3'-UTR, were conducted as follows.

MDBK cells were transformed with the above expression constructs using the DEAE-dextran method as described in Materials and Methods. Transiently transfected cell cultures were washed twice to remove serum and incubated at either 37° C. or 43° C. in a minimal volume (5 ml/75 $cm^2$) of serum-free MEM or OptiMEM I (Gibco). At the end of the incubation period the medium was collected and centrifuged for 5 min at 2000×g to remove cells and debris. Medium was dialyzed and lyophilized to dryness. Samples were denatured, resolved by electrophoresis in 7.5% Miniprotean gels (Bio-Rad), and proteins detected by Western blotting. The primary antibody was a 1:2000 dilution of a pool of monoclonal antibodies against either BHV-1 gIII or gIV proteins (van Drunen-Littel-van den Hurk, S., et al. (1984) *Virology* 135:466–479; Hughes, G., et al. (1988) *Archives of Virology* 103:47–60). The secondary antibody was horseradish peroxidase-conjugated goat anti-mouse IgG.

The results of transient assays for expression and secretion of BHV-1 glycoproteins in MDBK cells are shown in FIG. 3. FIG. 3*a* shows expression of truncated gIII from plasmid p3KHSPG3HU. Lanes 1–5 represent analysis of cell culture media added to washed cells at the start of the time interval (described below). Lanes 6–9 represent analysis of 10% of cell extracts. Lanes 1 and 6 show untransfected cells; lanes 2 and 7: 37° C., 3 h; Lanes 3 and 8: 43° C., 3 h; lane 4: 43° C., 3 h, after which cells were washed and subjected to 37° C., 2 h; lanes 5 and 9: 43° C., 6 h. The four prominent marker bands (non-numbered lanes) correspond to 116, 97, 66 and 45 kDa biotinylated molecular weight markers detected with avidin-horseradish peroxidase. Basal level synthesis was barely detectable (lane 2) but up-shift to 43° C. produced a significant amount of gIII in the medium (lane 3). There was more gIII protein in the medium after 6 h at 43° C. (lane 5) than after 3 h, indicating that the process of secretion continued beyond 3 h at 43° C. Secretion appeared to be efficient, since cellular extracts examined in lanes 6–9 showed no evidence of intracellular accumulation of gIII.

The expression of truncated gIV from p3KHSPG4HU is shown in FIG. 3*b*. Lane 1 shows purified truncated gIV protein synthesized and secreted in a vaccinia virus expression system. Lanes 2–5 show MDBK cells transfected with p3KHSPG4HU. Cell culture media was assayed 24 h later. Cells were washed and incubated for 2 h at 37° C. (lanes 2 and 4) or 43° C. (lanes 3 and 5) in medium without (lanes 2 and 3) or with (lanes 4 and 5) 2.5 μg/ml Brefeldin A. Cells were preincubated for 1 h in the drug prior to incubation at 37° C. or 43° C. The rate of incorporation of $^{35}$S-methionine into acid-precipitable material was unaffected by concentrations of Brefeldin A as high as 8 μg/ml. The four prominent marker bands (non-numbered lanes) correspond to 116, 97, 66 and 45 kDa biotinylated molecular weight markers detected with avidin-horseradish peroxidase. Again the basal level of synthesis was barely detectable (lane 2). An up-shift to 43° C. for 3 h caused a dramatic increase in the amount of the protein in the medium (lane 3). Lanes 4 and 5 show that the presence of gIV in the medium is actually the result of secretion and not the detachment and lysis of cells since Brefeldin A, a specific inhibitor of transport between the endoplasmic reticulum and Golgi apparatus, blocks this process (lanes 4 and 5). The band that appears immediately above gIV in lanes 2–5 is residual bovine serum albumin that is not removed by washing the cells.

EXAMPLE 4

Protracted Regulated Expression and Secretion of BHV-1qIII and gIV from MDBX Cells Stably Transfected with Plasmids pG3HUNEO and pG4HUNEO The expression and secretion of gIII and gIV from plasmids pG3HUNEO and pG4HUNEO (ATCC Accession Nos. 69075 and 69076, respectively), from Example 2, was tested as follows. These plasmids include the coding sequences for truncated gIII and gIV, respectively, driven by the bovine hsp70A promoter and 5'-UTR, a human hsp70A 3'-UTR and a cassette coding for aminoglycoside phosphotransferase.

MDBK cells were transfected and treated as described above to generate stable cell lines resistant to G418. Equal numbers of drug-resistant clones were obtained with each construct. After incubation at either 37° C. or 43°, as described, medium from the stably transfected clones was concentrated 4-fold for gel analysis (FIG. 4*a*) or left undiluted (FIG. 4*b*, table 1). A dot-immunoblot assay was conducted on the medium. Of 160 neomycin-resistant clones tested, 100 were found to be heat inducible for glycoprotein synthesis and secretion. The remainder were negative at both temperatures. Clones varied in the amount of glycoprotein produced as well as in the ratio between basal and induced protein levels. No differences were observed between the distribution of expression phenotypes for gIII- and gIV-producing clones. The induction properties of 7 gIV-producing clones were followed through 80 cell doublings with no noticeable change.

One gIV clone, designated MG4-57, was tested for synthesis and secretion of glycoprotein over a protracted time period. Clone MG4-57 was grown to confluence in 4% serum containing culture medium in a 150 cm² flask (4×10⁷ cells) and the flask was incubated with 10 ml serum-free medium at 43° C. for 6 h every day for 8 days denoting 8 cycles. This medium was tested for yield of gIV as shown in FIG. 4. The culture produced gIV in a quantity of 75 μg/150 cm² (4×10⁷ cells) for each 6 h period at 43° C. and the ability to synthesize and secrete gIV did not decrease even after 8 cycles. Qualitatively similar results were observed in a parallel experiment with a gIII-secreting clone. Subsequent experiments indicate that lowering the temperature back to 37° C. does not result in an immediate cessation of synthesis of gIV by the MG4-57 cell line. Consequently, best yields are obtained by performing a 6 h, 43° C. heat shock once in every 24 h, keeping the cells in serum-free medium throughout, and changing the medium once every 24 h (immediately prior to heat shock). This medium contains gIV at a level of 10–15 μg/ml and the experiment has been extended as far as 21 days. Total yield is thus 21 days×13 mls×10–15 μg/ml=3–4 mg per 150 cm² flask, or 4×10⁷ cells.

These results and those in Example 3 show that the bovine hsp70A gene is functional in the heat regulated expression of recombinant BHV-1 glycoproteins and thus is not a bovine heat shock cognate or pseudogene. The results also show that the constructs respond, in transient transfections, to both increases and decreases in temperature. Stably-transfected cell lines made with these constructs show a high proportion of clones with heat regulatable expression.

EXAMPLE 5

Antigenic Authenticity of gIV Produced by Expression Plasmid pG4HUNEO

The truncated gIV secreted by stably-transfected MDBK cells described in Example 4 was reacted with a panel of monoclonal antibodies directed against both continuous and discontinuous epitopes of full length gIV (van Drunen-Little-van den Hurk, S., et al. (1984), supra; Hughes, G., et al. (1988), supra). The results are shown in Table 1.

TABLE 1

Reactivity of Monoclonal Antibodies with Full-Length and Truncated gIV.

| MAb[a] | Epitope Specificity[b] | Neutralizing Activity[c] | ELISA Titer[d] | | |
|---|---|---|---|---|---|
| | | | VVgIV | VVΔIV | hspΔIV |
| 135 | Ia | ++ | 640 | 1280 | 1280 |
| 9D6 | Ib | + | 640 | 640 | 1280 |
| 3E7 | II | + | 160 | 160 | 160 |
| 10C2 | IIIa | ++ | 320 | 320 | 160 |
| 4Cl | IIIb | + | 320 | 320 | 160 |
| 2C8 | IIIc | ++ | 160 | 40 | 80 |
| 3Cl | IIId | ++ | 80 | 80 | 80 |
| 3DpS | IV | – | 1280 | 640 | 320 |

[a]Monoclonal antibodies developed by Hughes, G., et al.(1988) Archives of Virology 103:47–60.
[b]gIV epitopes assigned by competitive binding assays (Hughes, et al., supra).
[c]Neutralizing antibody titers determined for ascites fluids. - titer: <100; + titer: >100; ++ titer: >10,000 (Hughes, et al., supra).
[d]Antigen titer was expressed as the reciprocal of the highest dilution of glycoprotein IV giving a reading of at least 0.05 O.D. (492 nm). A 1:10 dilution corresponds to 0.04 μg of glycoprotein IV per well. VVgIV = affinity purified full-length gIV produced in vaccinia virus-infected BSC-1 cells and suspended in OptiMEM I medium (GIBCO) (van Drunen Littel-van den Hurk et al. Vaccine, in press). VVΔIV = affinity-purified truncated gIV produced in vaccinia virus-infected BSC-1 cells and suspended in OptiMEM. hspΔIV = truncated gIV, expressed under Hsp70A promoter and secreted in OptiMEM by transfected MDBK cells.

The reactivity was not significantly different from that of truncated and full-length gIV produced in a vaccinia virus expression system. The latter two proteins have been compared to authentic full-length BHV-1 gIV, field-tested in cattle, and found to be highly protective against BHV-1 infection (Van Drunen-Littel-van den Hurk, S., et al., Vaccine, In Press).

Several reports suggest that BHV-1 gIV has cytotoxic properties based on observations that it is very difficult to isolate stably-transfected cell lines expressing the native form of this protein (Fehler, F., et al. (1992) *J. Virol.* 66:831–839). Even though the hsp70A promoter shows some basal activity at 37° C. (see Example 3), the cytotoxicity of the product was overcome by using a truncated secreted form of the protein. No difference was observed in the number of stable clones and their inducible expression properties between constructs expressing gIII and gIV. While not wishing to be bound by theory, it is postulated that the cytotoxicity of gIV is either dependent on its location in the membrane or on the maintenance of a configuration that is lost in the truncated form. However, as demonstrated herein, the reactivity of the protein with several monoclonal antibodies is not substantially altered, suggesting that it is an effective vaccine immunogen.

In summary, the expression system has several important practical advantages for the production of vaccines. A single 150 $cm^2$ flask of $4\times10^7$ stationary-phase cells can produce approximately 3 to 4 mg of antigen (about 250 doses) with minimal manipulations involving temperature shifts and media collection. Production is still linear after 8 temperature-shift cycles, so that extension and optimization of the protocol will likely improve yields. This result also demonstrates that the transfected cells can be maintained in stationary phase, for protracted periods, while fully retaining the capacity to produce the recombinant protein. In comparison, a vaccinia/BSC-1 system based on a consensus strong late viral promoter, which is one of the most productive mammalian-based expression systems available, produced only twice this amount of secreted gIV (van Drunen-Little-van den Hurk, in press, supra).

EXAMPLE 6

Construction of an Alternative BHV-1 Expression Plasmid Utilizing a Drosophila 3'-UTR An expression plasmid was constructed as above, using the truncated BHV-1 gIII gene and a Drosophila melanogastor hsp70 3'-UTR, derived from pl73OR (Voellmy, R., et al. (1985) *Proc. Natl. Acad. Sci. USA* 82:4949–4953) in place of the human 3'-UTR. The resulting plasmid, pGIIIADU, comprising the bovine hsp70A promoter and 5'-UTR, the truncated gIII gene and the *D. melanogastor* 3'-UTR, was transfected into MDBK cells as described in Example 3. The cultures were heat shocked at 24 hrs post-transfection and media and cell extracts analyzed by Western blotting, as described in Example 3.

All of the detectable gIII was found in the medium, indicating that the protein was indeed expressed and secreted. A low basal level of synthesis of gIII at 37° C. was also seen. Shifting the cells to 43° C. resulted in a large induction of synthesis and secretion, presumably due to the efficient induction of transcription and translation driven by the bovine hsp70A promoter and associated 5'-UTR. Secretion proceeded efficiently at 43° C. for at least 3 to 6 hrs. This experiment shows that the bovine hsp70A promoter and 5'-UTR, along with the *D. melanogastor* 3'-UTR, effectively direct regulated expression of a BHV-1 glycoprotein in transformed cells.

EXAMPLE 7

Heat Regulated Synthesis of E. coli β-galactosidase

The ability of the bovine hsp70A promoter to express a procaryotic protein was tested using the E. coli Lac Z gene. Plasmids were constructed by cloning the SalI-NcoI fragment that incorporates the ATG initiation codon of the hsp70A gene shown in FIG. 1b, as described above, into plasmid pPOL26 (George, H. J., et al., (1987) Biotechnology 5:600–603) containing the Lac Z sequence. The coding sequence was immediately followed by a translation stop codon and the SV40 small t intron and polyadenylation signal. This construct was introduced into MDBK cells by DEAE dextran-mediated DNA transfection, as described above. β-galactosidase production was monitored histochemically by the addition of X-gal to fixed cells and by assay of β-galactosidase activity in cell extracts. The experiments showed that the bovine hsp70 promoter directed the production of amounts of β-galactosidase twenty-fold higher than those produced by plasmids utilizing the SV40 early promoter for the same purpose.

EXAMPLE 8

Expression of BVDV qp53 Using the Hsp70 Promoter

BVDV is a positive stranded RNA virus. Accordingly, the gene was cloned by reverse transcription of RNA prepared from infected cells, followed by a polymerase chain reaction to amplify the DNA. PCR primers were designed so as to provide an NcoI site incorporating a start codon in front of amino acid 665 of the NADL strain sequence, and a stop codon and a SalI site after amino acid 1036. This DNA was inserted into pG4HUNEO in place of the BHV-1 gIV coding sequence. The resulting plasmid, designated pGP53HUNEO was transfected into bovine MDBK cells.

Thus, a novel bovine hsp70 promoter and the use of the promoter in efficient expression systems have been described. Although preferred embodiments of the subject invention have been described in some detail, it is to be understood that obvious variations can be made without departing from the spirit and the scope of the invention as defined by the appended claims.

Deposits of Strains Useful in Practicing the Invention

A deposit of biologically pure cultures of the following strains was made with the international depository authority, American Type Culture Collection, 10801 University Boulevard, Manassas, Va. 20110-2209 pursuant to the terms of the Budapest Treaty. The accession number indicated was assigned after successful viability testing, and the requisite fees were paid. Access to said cultures and information pertaining thereto will only be given to those authorities, natural persons or legal entities entitled therto under Rule 11 of the Budapest Treaty and subject to the conditions as provided in that Rule. The above cultures were deposited under conditions which assure that access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. The designated deposits will be maintained for a period of at least thirty (30) years from the date of deposit, or for five (5) years after the last request for the deposit. Should a culture become nonviable or be inadvertently destroyed, or, in the case of plasmid-containing strains, lose its plasmid, it will be replaced with a viable culture(s) of the same taxonomic description.

These deposits are provided merely as a convenience to those of skill in the art, and are not an admission that a deposit is required under 35 USC §112. The nucleic acid sequences of these plasmids, as well as the amino sequences of the polypeptides encoded thereby, are incorporated herein by reference and are controlling in the event of any conflict with the description herein. A license may be required to make, use, or sell the deposited materials, and no such license is hereby granted.

| Strain | Deposit Date | ATCC No. |
|---|---|---|
| pG3HUNEO (in E. coli) | 9/29/92 | 69075 |
| pG4HUNEO (in E. coli) | 9/29/92 | 69076 |

---

We claim:

1. An isolated bovine hsp70A promoter capable of directing the transcription of a heterologous coding sequence positioned downstream therefrom, wherein said promoter is selected from the group consisting of (a) a promoter comprising the nucleotide sequence depicted at nucleotide positions 350 to 441, inclusive, of the upper strand of FIG. 2 (SEQ ID NO:1); (b) a promoter comprising the nucleotide sequence depicted at nucleotide positions 265 to 441, inclusive, of the upper strand of FIG. 2 (SEQ ID NO:1); (c) a promoter comprising the nucleotide sequence depicted at nucleotide positions 1 to 441, inclusive, of the upper strand of FIG. 2 (SEQ ID NO:1); and (d) a promoter comprising a nucleotide sequence that hybridizes to the promoter of (a), (b) or (c) in a Southern hybridization reaction performed under stringent conditions.

2. The promoter of claim 1 wherein said promoter comprises the nucleotide sequence depicted at nucleotide positions 350 to 441, inclusive, of the upper strand of FIG. 2 (SEQ ID NO:1).

3. The promoter of claim 1 wherein said promoter comprises the nucleotide sequence depicted at nucleotide positions 265 to 441, inclusive, of the upper strand of FIG. 2 (SEQ ID NO:1).

4. The promoter of claim 1 wherein said promoter comprises the nucleotide sequence depicted at nucleotide positions 1 to 441, inclusive, of the upper strand of FIG. 2 (SEQ ID NO:1).

5. An isolated bovine hsp70A 5'-untranslated region.

6. A recombinant expression construct effective in directing the transcription of a selected coding sequence, said expression construct comprising:
   (a) bovine hsp70A control sequences comprising a bovine hsp70A promoter according to claim 1; and
   (b) a coding sequence operably linked to said control sequences, whereby said coding sequence can be transcribed and translated in a host cell, and at least one of said control sequences is heterologous to said coding sequence.

7. The recombinant expression construct of claim 6 wherein said bovine hsp70 control sequences comprise a bovine hsp70A promoter and an hsp70 5'-untranslated region.

23

8. The recombinant expression construct of claim 7 wherein said bovine hsp70A promoter comprises the nucleotide sequence depicted at nucleotide positions 350 to 441, inclusive, of the upper strand of FIG. 2 (SEQ ID NO:1).

9. The recombinant expression construct of claim 7 wherein said bovine hsp70A promoter comprises the nucleotide sequence depicted at nucleotide positions 265 to 441, inclusive, of the upper strand of FIG. 2 (SEQ ID NO:1).

10. The recombinant expression construct of claim 7 wherein said bovine hsp70A promoter comprises the nucleotide sequence depicted at nucleotide positions 1 to 441, inclusive, of the upper strand of FIG. 2 (SEQ ID NO:1).

11. The recombinant expression construct of claim 7 wherein said hsp70 5'-untranslated region comprises a bovine hsp70A 5'-untranslated region.

12. A recombinant expression construct comprising:
(a) a nucleic acid molecule that comprises a coding sequence for a selected polypeptide; and
(b) hsp70 control sequences operably linked to said nucleic acid molecule, whereby said coding sequence will be transcribed and translated when in a host cell to produce said selected polypeptide, and at least one of said control sequences is heterologous to said coding sequence,
wherein said hsp70 control sequences comprise a bovine hsp70A promoter according to claim 1, a bovine 5'-untranslated region positioned downstream of said promoter and a 3'-untranslated region positioned downstream of said coding sequence.

13. The recombinant expression construct of claim 12 wherein said 3'-untranslated region is an hsp70 3'-untranslated region.

14. The recombinant expression construct of claim 13 wherein said hsp70 3'-untranslated region comprises a human hsp70 3'-untranslated region.

15. The recombinant expression construct of claim 13 wherein said hsp70 3'-untranslated region comprises a Drosophila hsp70 3'-untranslated region.

16. The recombinant expression construct of claim 13 wherein said hsp70 3'-untranslated region comprises a bovine hsp70 3'-untranslated region.

17. The recombinant expression construct of claim 12 wherein said coding sequence encodes an immunogenic bovine herpesvirus type 1 (BHV-1) gIII polypeptide.

18. The recombinant expression construct of claim 12 wherein said coding sequence encodes an immunogenic bovine herpesvirus type 1 (BHV-1) gIV polypeptide.

19. The recombinant expression construct of claim 12 wherein said coding sequence encodes an immunogenic bovine viral diarrhea virus (BVDV) gp53 polypeptide.

20. A recombinant expression construct effective in directing the transcription of a selected coding sequence, said expression construct comprising:
(a) bovine hsp70A control sequences comprising the nucleotide sequence depicted at nucleotide positions 1 to 666, inclusive, of the upper strand of FIG. 2 (SEQ ID NO:1), or a nucleotide sequence that hybridizes thereto in a Southern hybridization reaction performed under stringent conditions; and
(b) a coding sequence operably linked to said control sequences, whereby said coding sequence can be transcribed and translated in a host cell, and at least one of said control sequences is heterologous to said coding sequence.

24

21. A recombinant expression construct comprising:
(a) a nucleic acid molecule that comprises a coding sequence for a selected polypeptide; and
(b) hsp70 control sequences operably linked to said nucleic acid molecule and a 3'-untranslated region positioned downstream of said coding sequence, whereby said coding sequence will be transcribed and translated when in a host cell to produce said selected polypeptide, and at least one of said control sequences is heterologous to said coding sequence,
wherein said hsp70 control sequences comprise the nucleotide sequence depicted at nucleotide positions 1 to 666, inclusive, of the upper strand of FIG. 2 (SEQ ID NO:1).

22. The recombinant expression construct of claim 21 wherein said 3'-untranslated region is an hsp70 3'-untranslated region.

23. The recombinant expression construct of claim 22 wherein said hsp70 3'-untranslated region comprises a human hsp70 3'-untranslated region.

24. The recombinant expression construct of claim 22 wherein said hsp70 3'-untranslated region comprises a Drosophila hsp70 3'-untranslated region.

25. The recombinant expression construct of claim 22 wherein said hsp70 3'-untranslated region comprises a bovine hsp70 3'-untranslated region.

26. The recombinant expression construct of claim 23 wherein said coding sequence encodes an immunogenic bovine herpesvirus type 1 (BHV-1) gIII polypeptide.

27. The recombinant expression construct of claim 23 wherein said coding sequence encodes an immunogenic bovine herpesvirus type 1 (BHV-1) gIV polypeptide.

28. The recombinant expression construct of claim 23 wherein said coding sequence encodes an immunogenic bovine viral diarrhea virus (BVDV) gp53 polypeptide.

29. A host cell stably transformed with the recombinant expression construct of claim 6.

30. A host cell stably transformed with the recombinant expression construct of claim 20.

31. A host cell stably transformed with the recombinant expression construct of claim 26.

32. A host cell stably transformed with the recombinant expression construct of claim 27.

33. A host cell stably transformed with the recombinant expression construct of claim 28.

34. The host cell of claim 29 wherein said cell is a thermotolerant cell.

35. The host cell of claim 30 wherein said cell is a thermotolerant cell.

36. The host cell of claim 34 wherein said thermotolerant cell is a Madin-Darby bovine kidney (MDBK) cell.

37. The host cell of claim 35 wherein said thermotolerant cell is a Madin-Darby bovine kidney (MDBK) cell.

38. A method of producing a recombinant polypeptide comprising:
(a) transforming a thermotolerant mammalian host cell with a recombinant expression construct according to claim 12, and
(b) treating said transformed cell with heat, under conditions whereby said coding sequence for said selected polypeptide is expressed, thereby producing said recombinant polypeptide.

39. A method of producing a recombinant polypeptide comprising:

(a) transforming a thermotolerant mammalian host cell with a recombinant expression construct according to claim 21; and (b) treating said transformed cell with heat, under conditions whereby said coding sequence for said selected polypeptide is expressed, thereby producing said recombinant polypeptide.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 750 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
TCTTCGAGAA ACTCGGGAAC TTTCTGTATT TTGGCTGTCC CGGCAGTCGT GTAGCCCTTA          60

ATTCTACTTT AAACCACCAA ACTAATTTGA GCCCCGAGAT CCTCTCACCG CCCTACAATT         120
```

```
AATTACAAGC CCAGGGCTGA TCCTTCCAGT CGACTCGACT CCAAACTACT TGGCTGGCTG      180

GTCGCCAGGA AACCAGAGAC AGAGTGGGTG GACCTTCCCA GCCCCTCTCC CCCTCTCCTT      240

AGGACTCCTG TTTCCTCCAG CGAATCCTAG AAGAGTCTGG AGAGTTCTGG GAGGAGAGGC      300

ATCCAGGGCG CTGATTGGTT CCAGAAAGCC AGGGGGCAGG ACTTGAGGCG AAACCCCTGG      360

AATATTCCCG ACCTGGCAGC CCCACTGAGC TCGGTCATTG GCTGACGAGG GAAAAGGCGG      420

GGCTTGATGA AGAATTATAA ACACAGAGCC GCCTGAGGAG AAACAGCAGC CTGGAGAGAG      480

CTGATAAAAC TTACGGCTTA GTCCGTGAGA GCAGCTTCCG CAGACCCGCT ATCTCCAAGG      540

ACCGCCCGAG GGGCACCAGA GCGTTCAGTT TTCGGGTTCC GAAAAGCCCG AGCTTCTCGT      600

CGCAGATCCT CTTCACCGAT TTCAGGTTTG AAGCTTATTT CGGAGCCGGA AAAGCAGGGC      660

ACCGGCATGG CGAAAAACAC AGCTATCGGC ATCGACCTGG GCACCACCTA CTCCTGCGTA      720

GGGGTGTTCC AGCACGGCAA GGTGGAGATC                                      750

(2) INFORMATION FOR SEQ ID NO:2:

(i) SEQUENCE CHARACTERISTICS:
        (A) LENGTH: 533 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

TTCCTCTCAG GGTCCCTGTC CCCTCCAGTG AATCCCAGAA GACTCTGGAG AGTTCTGAGC       60

AGGGGGCGGC ACTCTGGCCT CTGATTGGTC CAAGGAAGGC TGGGGGGCAG GACGGGAGGC      120

GAAACCCCTG GAATATTCCC GACCTGGCAG CCTCATCGAG CTCGGTGATT GGCTCAGAAG      180

GGAAAAGGCG GGTCTCCGTG ACGACTTATA AAAGCCCAGG GGCAAGCGGT CCGGATAACG      240

GCTAGCCTGA GGAGCTGCTG CGACAGTCCA CTACCTTTTT CGAGAGTGAC TCCCGTTGTC      300

CCAAGGCTTC CCAGAGCGAA CCTGTGCGGC TGCAGGCACC GGCGCGTCGA GTTTCCGGCG      360

TCCGGAAGGA CCGAGCTCTT CTCGCGGATC CAGTGTTCCG TTTCCAGCCC CCAATCTCAG      420

AGCCGAGCCG ACAGAGAGCA GGGAACCGCA TGGCCAAAGC CGCGGCAGTC GGCATCGACC      480

TGGGCACCAC CTACTCCTGC GTGGGGGTGT TCCAACACGG CAAGGTGGAG ATC            533
```